US007326181B2

(12) United States Patent
Katims (10) Patent No.: US 7,326,181 B2
(45) Date of Patent: Feb. 5, 2008

(54) NERVOUS TISSUE STIMULATION DEVICE AND METHOD

(76) Inventor: Jefferson Jacob Katims, 6637 Charlesway, Towson, MD (US) 21204

( * ) Notice: Subject to any disclaimer, the term of this patent is extended or adjusted under 35 U.S.C. 154(b) by 385 days.

(21) Appl. No.: 10/788,271

(22) Filed: Mar. 1, 2004

(65) Prior Publication Data

US 2005/0192567 A1    Sep. 1, 2005

Related U.S. Application Data

(63) Continuation of application No. 09/858,644, filed on May 17, 2001, now abandoned.

(60) Provisional application No. 60/205,073, filed on May 18, 2000.

(51) Int. Cl.
*A61N 1/36* (2006.01)
*A61B 5/05* (2006.01)

(52) U.S. Cl. .......................................... 600/554; 607/46

(58) Field of Classification Search ...................... None
See application file for complete search history.

(56) References Cited

U.S. PATENT DOCUMENTS

| 5,061,234 A * | 10/1991 | Chaney ........................ 600/14 |
| 5,284,154 A * | 2/1994 | Raymond et al. ........... 600/554 |
| 5,806,522 A * | 9/1998 | Katims ........................ 600/554 |
| 2002/0055688 A1* | 5/2002 | Katims ........................ 600/554 |

* cited by examiner

*Primary Examiner*—Kristen D. Mullen
(74) *Attorney, Agent, or Firm*—Millen, White, Zelano & Branigan, P.C.

(57) ABSTRACT

A method using a precisely controlled, computer programmable stimulus for neuroselective tissue stimulation that does not leave a sufficient voltage or electrical artifact on the tissue being stimulated that would interfere or prevent a monitoring system from recording the physiological response is utilized to evaluate the physiological conduction of the tissue being studied. A computer controls both the waveform, duration and intensity of the stimulus. An output trigger to the nerve response recording component controls the timing of its operation. A neuroselective nervous tissue response latency and amplitude may be determined. The computer controlled stimulus may also be administered for therapeutic purposes.

19 Claims, 12 Drawing Sheets

NERVOUS TISSUE STIMULATION DEVICE AND METHOD

This application is a continuation of U.S. 09/858,644, filed on May 17, 2001, now abandoned, and claims priority to U.S. provisional application 60/205,073, filed on May 18, 2000.

FIELD OF THE INVENTION

This invention relates to a method and apparatus for neuroselective nerve conduction stimulation which permits neuroselective nerve response monitoring which enhances the utility of the diagnostic or therapeutic procedure which pertains to the neurological condition of an individual an animal or isolated nervous tissue being evaluated. Nervous tissue includes nerves and is defined for the purposes of this specification as any living tissue with electro-responsive characteristics. This would include tissues such as muscle tissue which is electronically reactive.

BACKGROUND OF THE INVENTION

The measurement of the function of nerves and nervous tissue by assessing their ability to transmit impulses provides valuable diagnostic information for the practice of medicine, surgery, chiropractic and other health fields and biological research. Metabolic, toxic, compressive and other types of nerve damage, the effects of interventions including pharmaceuticals and also nerve regeneration may be assessed using this information.

The nerve conduction velocity and amplitude evaluation traditionally utilizes electronic or electromagnetic stimulation of nervous tissue or nerve fibers to evoke a physiological response which is conducted along the length of the nervous tissue. This physiological response is recorded at a distant site on the nerve or the tissue innervated by this nerve such as muscle tissue. The nervous tissue response to this stimulus is recorded using an extremely sensitive electromagnetic amplifier. The distance between the site of stimulation and response recording is divided by the latency of the amplified recorded response time from the time of the stimulus to determine the Nerve Conduction Velocity (NCV) of this segment of the nerve. The amplitude of the recorded signal provides information regarding the actual number of nerve fibers responding.

Peripheral nerves are composed of individual nerve fibers if varying diameters. There are three major subpopulations of peripheral nerve fibers based on characterization of their fiber diameter. Any one of these subpopulations may become effected in a disease condition. Assessing the integrity of all three sub-populations or selectively stimulating these 3 populations of sensory nerve fibers is important for medical diagnostics, therapeutics and research purposes.

The nerves diameter also associated to its function. The largest diameter sensory nerve fibers are associated with sensation such as touch whereas the smaller diameter fibers are associated with pressure, temperature and pain sensations. The typical peripheral nerve is composed of large, middle and small diameter fibers that comprise <10%, <10% and >80% of the total number of fibers respectively. The larger the diameter of the nerve fiber, the greater its responsiveness to an electrical stimulus. The larger diameter nerve fibers have the fastest conduction velocity, the lowest electrical charge threshold and the shortest duration response signal (referred to as an Action Potential). A typical large diameter fiber has a conduction velocity of 50 m/s whereas a typical small diameter fiber has a conduction velocity of 1 m/s. The larger diameter fibers have greater numbers of ion channels per cross sectional surface area of exposed fiber in contrast with the smaller diameter nerve fibers which have the lowest number of ion channels per cross sectional surface area of exposed fiber. This difference in the cross sectional number of ion channels may contribute to the largest diameter fibers also having the briefest inter-response rest or refractory period of <0.4 msec in comparison to up to 20 msec in the smallest diameter fibers.

Presently existing technology for NCV evaluations utilizes a suprathreshold pulsed waveform of electrical or electromagnetic stimulus to evoke a nervous tissue response. A limitation of the presently existing technology is that it stimulates all of the nerve fibers in the peripheral nerve simultaneously.

Although the larger diameter nerve fiber comprises less than 10% of the typical peripheral sensory nerve's fibers, they make up >90% of the volume of the nerve. As a consequence of the large fibers comprising the bulk of the volume of the nerve, they contribute over >90% of the nerves response electrical potential from the combined Action Potentials (referred to as the Compound Action Potential, CAP) from all of the various diameter nerve fibers. The major contribution to electrical potential the CAP from the large diameter fibers drowns out the Action Potential signals from the smaller diameter fibers. As a result, the conventional NCV evaluation is limited in that it is primarily only capable of evaluating the function of the large diameter nerve fibers and at the same time because it stimulates all of the fibers in the nerve it is painful. Any medical test or procedure that is painful has poor patient compliance for initial and follow-up evaluations.

It is an aspect of the present invention to provide an electrical or electromagnetic stimulus that permits neuroselective NCV and amplitude measures to be obtained from the three major sub-populations of nerve fibers which will be much less painful and in-part painless in contrast with currently existing technology and result in superior patient compliance for evaluations than is possible using presently existing NCV technology.

It is also an aspect of the present invention to improve the therapeutic efficacy of interventions requiring precise nerve stimulation with or without nerve response monitoring equipment.

A pulsed waveform may be mathematically described by Fourier Analysis in terms of its harmonic components. These components may be described as related amplitude sine waves of specific harmonic frequencies. Previous research has demonstrated neuroselectivity of an electrical stimulus when it is administered in its harmonic components as a sinusoidal waveform as described in the following references:

1) Katims, J. J., Long, D. M., Ng, L.K.Y. Transcutaneous Nerve Stimulation (TNS): Frequency and Waveform Specificity in Humans. *Applied Neurophysiology*, Volume 49:86-91, 1986.
2) Katims, J. J. Electrodiagnostic Functional Sensory Evaluation of the Patient with Pain: A Review of the Neuroselective Current Perception Threshold (CPT) and Pain Tolerance Threshold (PTT). *Pain Digest* Volume 8(5), 219-230, 1998.

Figure 10:
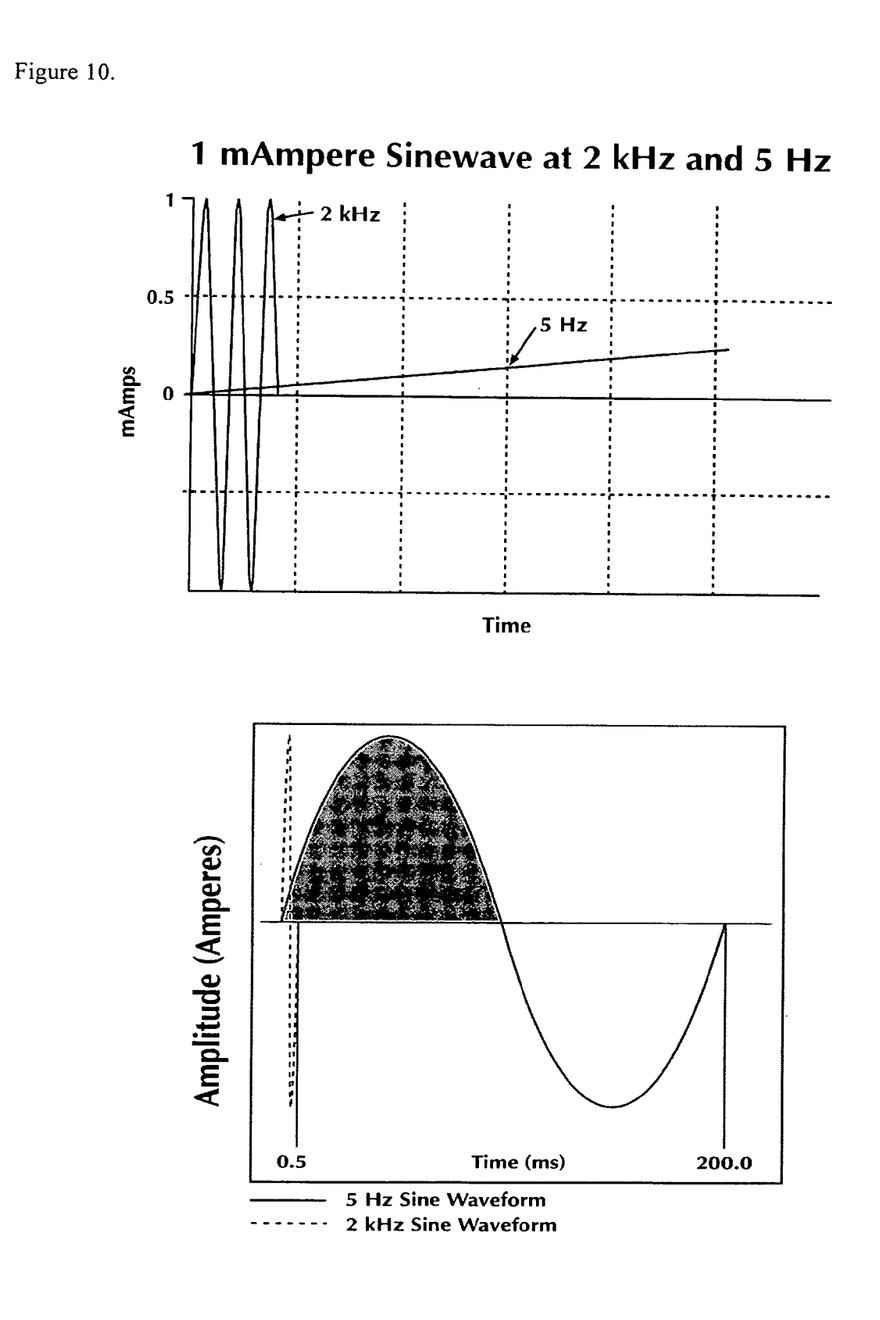
FIG. 10 Upper panel: Graph depicting 2 kHz and 5 Hz sinusoidal waveforms drawn to scale. Lower panel: Graph of amplitude vs time for the 2000 Hz and 5 Hz frequencies, depicting sinusoidal waveform.

It is believed that the slow rate of depolarization of a low frequency (eg. 5 Hz) sinusoid stimulus permits the large diameter nerve fibers, due to their fast responsiveness, to repolarize faster than the this slow stimulus can polarize them. Therefore the low frequency sine wave stimulus is not sufficient to bring the large diameter nerve fibers to their threshold potential. The large diameter fibers have a refractory period as brief as 0.4 msec and a small diameter fiber can have a refractory period as long as 20 msec. A period of 180° of a 2000 Hz sinewave is 0.25 msec and a 180° period of a 5 Hz sinewave is 100 msec in duration. This is illustrated in FIG. 10. The low frequency sinewave is of sufficient charge and duration to depolarize the small diameter nerve fibers to their threshold potential which enables them to generate action potentials in response to this stimulus. This low frequency sinusoid waveform stimulus has such a slow rate of depolarization that the large diameter rapidly responding nerve fibers can repolarize faster than this stimulus can depolarize it. In contrast, a 2000 Hz sinewave is too fast and has a relatively lower charge than the 5 Hz sinewave (approximately 400× less charge per 180° of stimulus). The differences between these two different frequency sinusoid waveforms is illustrated in FIG. 10.

Nervous tissue stimulation technology currently commercially available that is used for purposes of obtaining NCV measurements utilizes a square or pulsed waveform stimulus which, in contrast to a sinusoid or slowly rising waveform, has an almost instantaneous change in polarization. The most widely used methodology for conducting NCV studies routinely administers the stimulation at 150% of the intensity required to evoke a maximal response as observed using a response monitoring apparatus. This intensity this 150% supramaximal response stimulation causes a rapid change in the nerve tissue polarization and excites all the subpopulations of nerve fibers at the same time and therefore lacks the neuroselectivity of the sinusoid waveform of specific frequencies.

My previous patents, U.S. Pat. No. 4,503,863, No. 4,305, 102, and No. 5,806,522 describe a "Method and Apparatus for Transcutaneous Electrical Stimulation" using a continuous (i.e. of a duration over 0.5 seconds, much greater than 360° of a sinusoidal waveform constant alternating current stimulus of various frequencies for purposes including the determination of the neuroselective Current Perception Threshold (CPT) measurements using a non-invasive, non-aversive electrical stimulus applied at various frequencies. Work has continued in this direction endeavoring to develop this technology to construct a neuroselective nerve conduction velocity device. The technology described in these above cited CPT related patents was not compatible with currently existing commercially available EMG devices. The problem was that after administering an alternating current stimulus to the skin for approximately 0.5 seconds or more and then turning off the stimulus to permit recording of the nerves response, a voltage potential remained in the subjects body and drowned out the possibility of recording any nerve response from the response monitoring electrode. The reason for this voltage potential remaining on the subject is that there are inductive reactance properties of human skin which result in the applied voltage and current going out of phase.

It was necessary in the development that ensued leading up to the present invention to develop entirely new type electrodiagnostic apparatus for neuroselective of nerve stimulation. Examples of prior art nerve conduction electrical or electromagnetic response stimulator patents include the following are set out below:

| U.S. Pat. Nos. | Inventor(s) U.S. Patents | Issue Date |
|---|---|---|
| 4,807,643 | Rosier | Feb. 28, 1989 |
| 5,066,272 | Eaton, et al. | Nov. 19, 1991 |
| 5,143,081 | Young, et al. | Sept. 1, 1992 |
| 5,806,522 | Katims | Sept. 15, 1998 |
| 5,976,094 | Gozani | Nov. 2, 1999 |

SUMMARY OF THE INVENTION

It is an object of the present invention to overcome the deficiencies in the prior art.

It is another object of the present invention be able to provide a computer controlled electrical or electromagnetic stimulus signal that may be utilized to neuroselectively excite nerve fibers to generate responses that may be recorded by a nerve response recording component. The ability to record these responses permits the neuroselective determinations of the latency and amplitude of the nervous tissue response to the stimulus.

It is also an object of the present invention to employ programmable circuitry to generate the output wave form signal used to stimulate the nervous tissue.

It is also an object of the present invention to employ programmable circuitry to generate the output waveform signal used to stimulate the nervous tissue to be a 180° or a 360° sinusoid waveform stimulus. The present invention when utilizing a low frequency sinusoid waveform stimulus (eg., 5 Hz), operates optimally using a 360° sinusoid waveform stimulus as opposed to the 180° stimulus. The 360° stimulus has a relative positive and negative component that tend to cancel each other during monitoring by a physiological response monitoring system. The 5 Hz 180° sinusoid waveform has only a positive or a negative component alone. The 180° sinusoid waveform stimulus has sufficient unbalanced charge (positive or negative) effecting the response monitoring system to interfere with the actual monitoring of the physiological response. In contrast the 2000 Hz 180° sinusoid waveform stimulus does not produce sufficient charge to interfere with the functioning of standard physiological or nerve response monitoring systems.

It is also an object of the present invention to provide a neuroselective nervous tissue stimulator apparatus that may be used without leaving a voltage or electrical artifact on the tissue being stimulated that would interfere or prevent a monitoring system from recording the neurophysiological response.

It is also an object of the present invention to employ programmable circuitry to generate the output wave form stimulus used to stimulate the nervous tissue with rapidly increasing intensities and therefore rapidly depolarize the nervous tissue. This rapidly depolarizing stimulus permits the preferential stimulation of larger diameter nerve fibers or more responsive nervous tissue. Examples of such wave forms include a 1000 or 2000 Hz sinusoid or triangular shapes (monophasic or bi-phasic).

It is also an object of the present invention to employ programmable circuitry to generate the output wave form stimulus used to stimulate the nervous tissue with slowly increasing intensities and therefore slowly depolarizing the nervous tissue. This slowly depolarizing stimulus permits the preferential stimulation of smaller diameter nerve fibers of less reactive nerve tissue. Examples of such wave forms include a 5 Hz sinusoid, triangular or elliptical shapes.

It is also an object of the present invention to provide an output signal that may be repeatedly administered to permit a response monitoring system to conduct a signal averaging analysis.

It is also an object of the present invention to provide a neuroselective nervous tissue stimulator that may be used in conjunction with currently commercially available NCV, nervous tissue stimulator or the Current Perception Threshold (CPT) apparatus described in Katims U.S. Pat. No. 5,806,522.

It is also an object of the present invention to provide a neuroselective nervous tissue stimulator apparatus that may be used with the response recording component of currently commercially available Nerve Conduction Velocity (NCV) devices or may be included as a component of an NCV device with a response recording component.

It is also an object of the present invention to permit less painful motor and sensory NCV evaluations than are currently availably using the prior art technology. This feature enhances patient compliance for initial and follow-up evaluations.

It is also an object of the present invention to provide a neuroselective nervous tissue stimulator apparatus that may be controlled and monitored by an external computer.

It is also an object of the present invention to disclose a method and apparatus for electrical or electromagnetic nerve stimulation that is battery or line powered.

It is also an object of the present invention to disclose a method and apparatus for electrical or electromagnetic nerve stimulation that is capable of having its output waveform programed by use of a computer.

It is also an object of the present invention to permit discrete nervous tissue stimulation that does not interfere with nervous tissue response monitoring equipment where nervous tissue responses may be required for monitoring therapeutic interventions, or monitoring in situ of nerve responses for evaluating the response to a therapeutic intervention, for example blood concentrations of lidocaine or glucose.

It is also an object of the present invention to utilize the stimulus output for therapeutic purposes including nervous tissue stimulation that does not interfere with nervous tissue response monitoring equipment for pain relief including spinal cord stimulation, prosthetic nerve stimulation, therapeutic nervous tissue stimulation including the purposes of augmenting or attenuating normal or impaired nerve function.

It is also an object of the present invention to disclose a method and apparatus.

These advantages of the present system are critical and of importance, not only to the examination and to the examiner, but also to the patient, and the utility of nerve conduction stimulation will be enhanced over currently existing technology. In summary, the apparatus of the present invention enables neuroselective nerve stimulation that is not associated with a voltage charge remaining on the nervous tissue, or disrupting the physiological response monitoring system after the stimulus is turned off, that may be used for determinations of nerve conduction velocities and amplitudes that is impossible with the prior art devices. The greater amount of diagnostic information that is inherent in the present invention in the apparatus and in the method is a critical advantage to the great benefit of the patient and to the public being tested. Additionally the apparatus of the present invention may be used for therapeutic purposes.

METHOD DESCRIPTION

Device Operation

The apparatus of the present invention, being computer controlled, is capable of functioning in various output modes determined by the operator of the device through pressing switches on the control panel of the device related to mode selection. The mode selection of the present invention is for neuroselective conduction velocity and amplitude. This mode generates a 360° sinusoid at 3 different frequencies 2000 Hz, 250 Hz and 5 Hz. The example of the present invention includes an external nerve response monitoring system 34. This example also illustrates the present invention incorporated into a CPT device, FIG. 12. An example of this neuroselective conduction velocity and amplitude modes of operation follows:

Initial Start-up Mode

Figure 11:
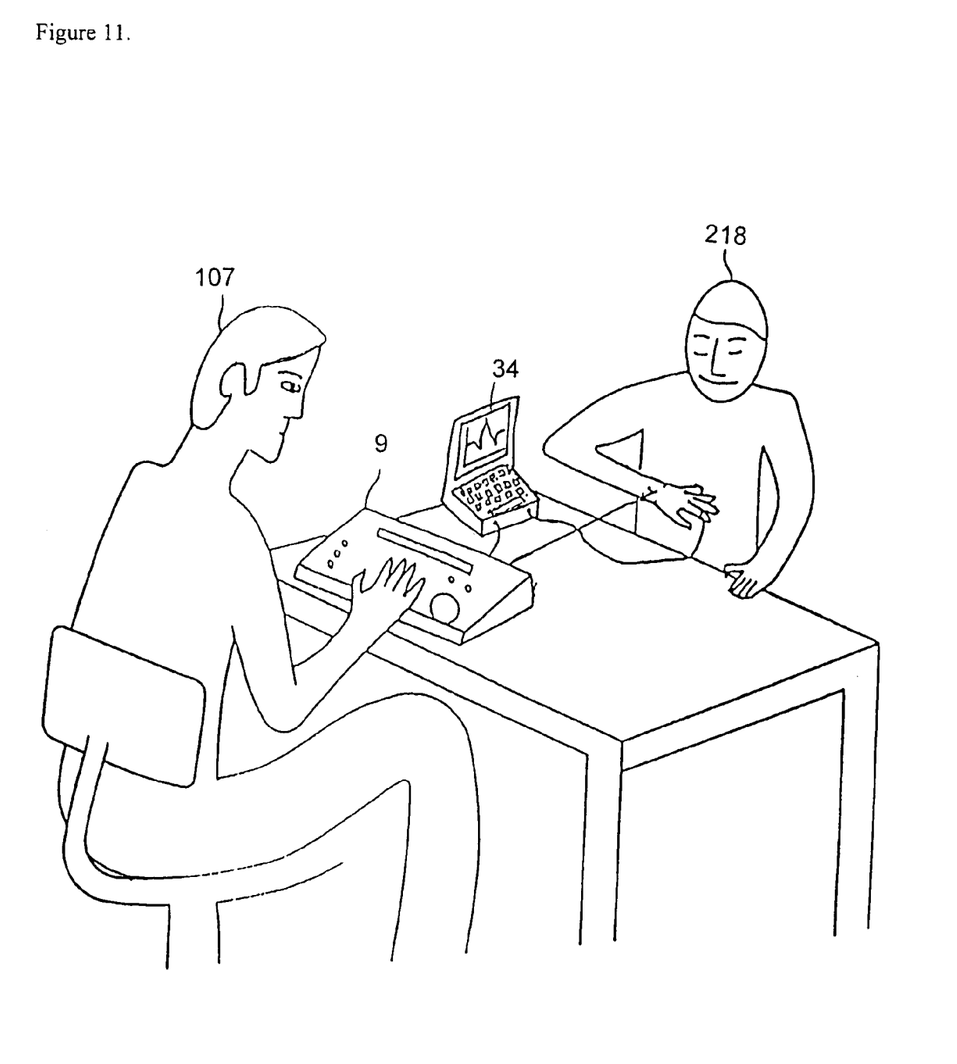
FIG. 11 is an illustration of the system of the present invention with stimulating electrodes placed over the subjects wrist crease, with a technician operating the device. The device is also connected to a nerve response monitoring system which is also connected to electrodes placed on the index finger of the patient.
Figure 12:
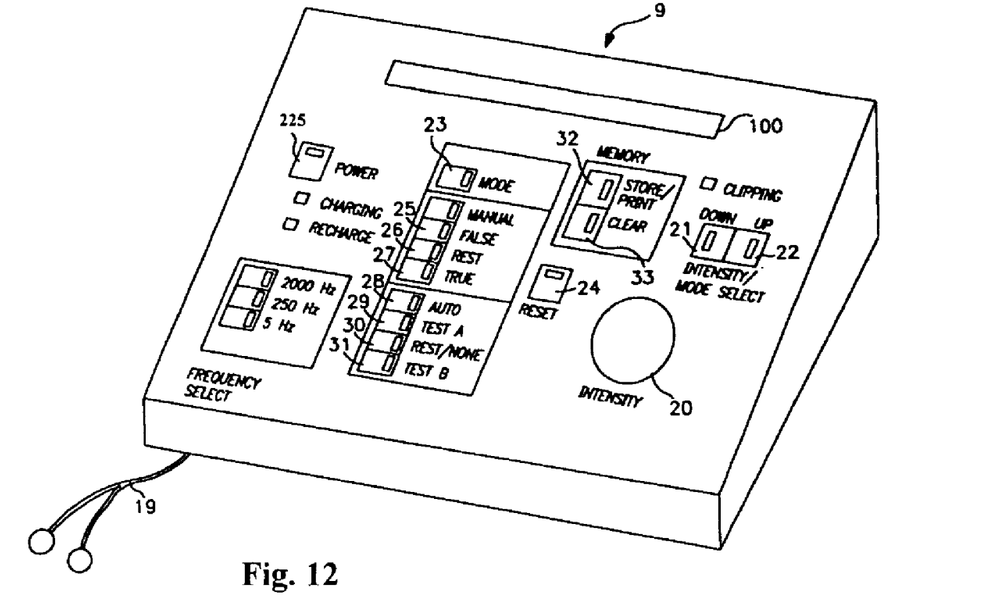
FIG. 12 is an illustration of the overall apparatus as it would appear when incorporated into a Current Perception Threshold (CPT) device.

After the technician 107 FIG. 11 presses the power button 225 FIG. 12 and turns on the device 9, the liquid crystal display 100 identifies the manufacturer of the device and any related information regarding identification of the device.

The text in the display 100 FIG. 12 under device control changes to guide the operator as to the various steps in using the stimulator including an electrode cable test.

The apparatus 9 FIG. 11 has its external trigger control connected to trigger input the external nerve response monitoring system 34. This external nerve response monitoring system 34 can be any presently commercially available nerve conduction device presently available with a functioning response monitoring system and external trigger control.

An example would be a standard nerve conduction velocity device or an EMG machine or an EEG machine or fMRI, PET or thermography imaging devices or other types of biological response monitor.

The device 9 electrodes 19 FIG. 12 are placed in the example in the illustration over the median nerve proximal to the wrist crease of the subject 218 FIG. 11 being tested. Monitoring electrodes from the external nerve response monitoring system 34 are placed on the distal phalange of the index finger of the subject 218. The technician 107 adjusts the intensity of the stimulus using intensity knob 20 FIG. 12 according to the criteria that is selected for the test, for example, the intensity may be set to the patients Current Perception Threshold (CPT) intensity (as described in U.S. Pat. No. 5,806,522) or some other value such as the maximum intensity evoked response as observed from the nerve response monitoring system 34 FIG. 1.

The external trigger output of the device signals the nerve response monitoring to monitor the response of the nerves being studied. In this example the monitored response signal will permit the conduction velocity and amplitude to be determined at the site of the monitoring electrodes of the right index finger subject 218 FIG. 1. Most commercially available NCV machines also permit signal averaging. The nerve responses evoked by the output signal of the present invention may be repeatedly studied by signal averaging techniques to obtain an averaged signal response if desired.

By using only a 360° sine wave signal there is not sufficient voltage remaining on the subject to interfere with any monitored response. This waveform overcomes the limitations imposed by the continuous sinewave stimulation and the lack of neuroselectivity of a pulse or square waveform stimulus and permits neuroselective nerve conduction responses to be studied using nerve response monitoring systems.

Apparatus Description

Figure 1:
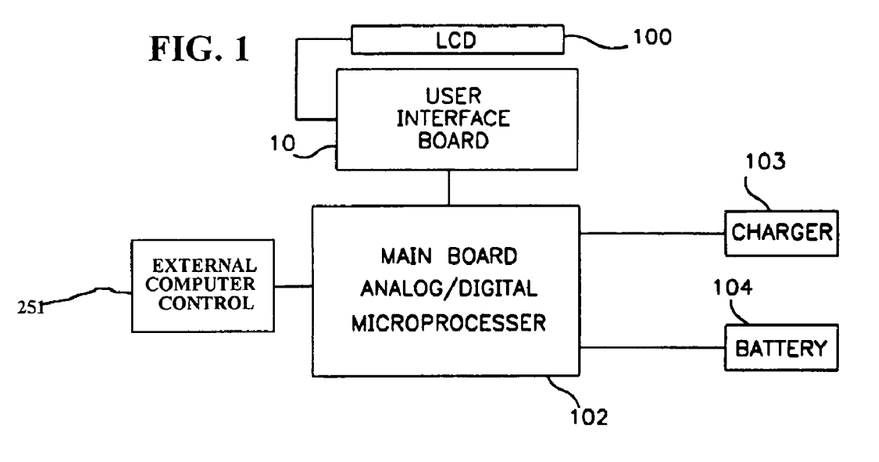
FIG. 1 is a block diagram illustration of the overall system.

Referring to FIG. 1, the apparatus consists of the main board 102, the user interface 10, Liquid Crystal Display 100, the charger 103 which is a commercially available stand alone unit (e.g. Tamara, Inc., Japan). There is also a charger section on the main board 102 shown in FIG. 8, for charging the battery 104. Alternatively a 6 volt power source derived from a line source may be employed instead of a battery.

Figure 2:
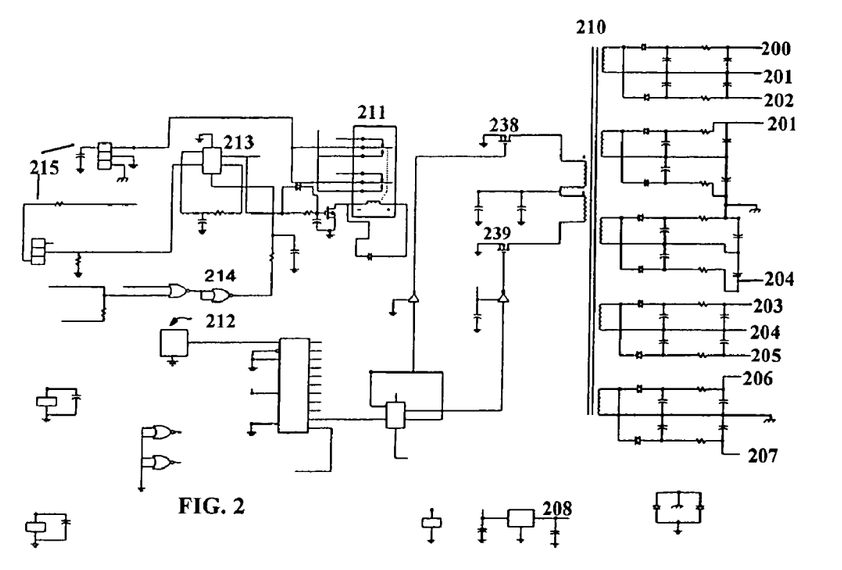
FIG. 2 is a schematic diagram of the power supply used in the system.

Referring to FIG. 1, the main board has a Power Supply Section (detailed in FIG. 2) that receives a 6-volt input from the battery 104. As a safety feature, the power supply FIG. 2 is inherently limited through the use of small MOSFETS 238 and 239 (on Resistance of 0.3 Ohms) and a small transformer 210 (<5 VA), thereby limiting the amount of power available at to the output. This provides an ultimate back-up safety feature. Under the failure of any other portions of this circuitry, there is not sufficient high voltage power available to harm the patient.

Power Supply Schematic FIG. 2 is a component of the main board 102. The power supply section produces the necessary voltages using a switching circuit with MOSFETS 238 and 239 to produce an AC input for the primary of transformer 210. After rectification and filtering on the secondary the following voltages are provided for the apparatus:

| Voltage | FIG. 2<br>Reference # |
|---------|------------|
| +150 | 200 |
| +135 | 201 |
| +120 | 202 |
| −120 | 203 |
| −135 | 204 |
| −150 | 205 |
| +14 | 206 |
| −14 | 207 |
| +5 | 208 |
| −5 | 209 |
| | (FIG. 4) |

The power supply FIG. 2 also has an on/off function. The actual power to the switching regulator FIG. 2 is passed through a relay 211. Relay 211 is controlled by an always-powered CMOS flip/flop 213. CMOS flip/flop 213 detects activation or depression of the power on button.

Referring to FIG. 2, the flip/flop 213 and associated logic circuitry 214 monitors the status of the charging jack 215. If the extra set of contacts in the charging jack 215 are opened by insertion of a plug, then the logic circuitry 214 resets the flip/flop 213 which forces the relay 211 to open and turn off the entire unit. This sequence may also be actuated by the micro-controller 216 illustrated in FIG. 3, this is the auto off function. The auto off function protects the battery from accidental discharge.

Figure 6:
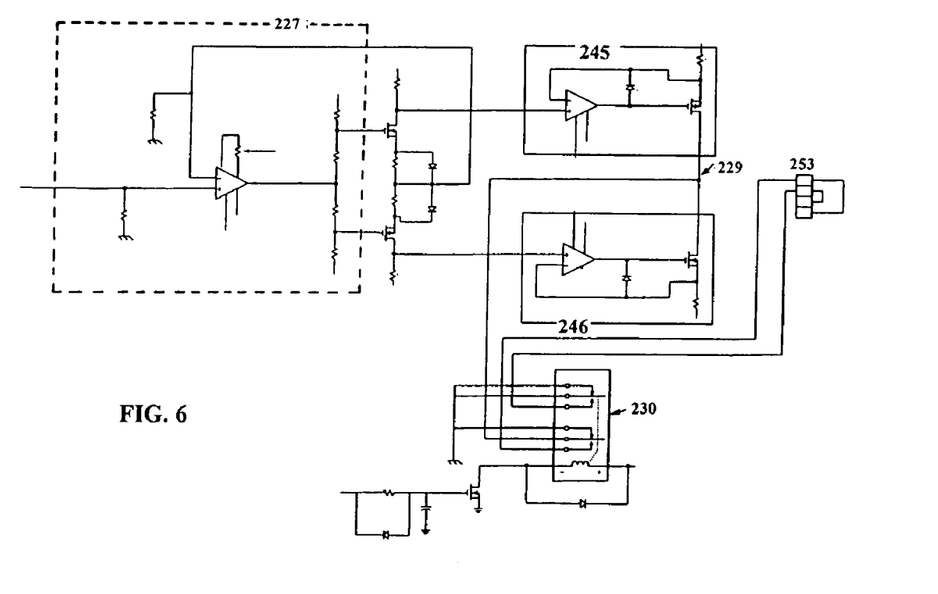
FIG. 6 is a schematic diagram of the MOSFET Output Stage used in the system.

Referring to FIG. 6, an additional safety feature is the use of separate relay 230 from the power supply relay 211 illustrated in FIG. 2. The control signal for output signal relay 230 FIG. 6 is switched on approximately one second after the power goes on. Relay 230 is switched off immediately when the on/off switch is pressed to turn the unit off, while the actual power for the unit goes off approximately one second after relay 230. Therefore, the output relay 230 is never closed when the power is turned on or turned off, thereby preventing accidentally discharging the electrical stimulus to the subject while turning the device on or off. This design ensures there are no start-up transients or turn-off transients. The output relay 230 FIG. 6 also interrupts the output ground. Therefore in the unlikely situation of the unit being hooked up to a failed and shorted charger 103, while the charger is plugged into an incorrectly wired wall outlet. Where the live and ground are switched, and a subject is connected who is also touching a ground there still will not be any hazard.

Referring to FIG. 2, the power supply is synchronized to the 2-megahertz quartz crystal 212, which is also used for one of the waveform generation systems as illustrated in FIG. 6. The frequencies are generated by dividing the 2 megahertz crystal 212 until you generate frequencies at 100 times the desired the output frequency. The 500 Hz signal is generated to create the 5 Hz sinewave. Also generated is a 25 kHz signal to generate the 250 Hz sinewave and a 200 kHz to generate the 2 kHz sinewave. The 100× signal is used to clock a switched capacitor filter 226 FIG. 4 and is then divided by 100 and provides an analog input to the switched capacitor filter 226 FIG. 4. The switched capacitor filter 226 FIG. 4 extracts the fundamental frequency from the divided signal. This feature produces a very clean sinewave, which upon inspection appears to have 100 timing steps. Since the same path is followed by all three frequencies, there are no amplitude variations. Additionally, since each frequency is traceable back to the quartz crystal, the accuracy is that of the original crystal 212 shown in FIG. 2.

Figure 3:
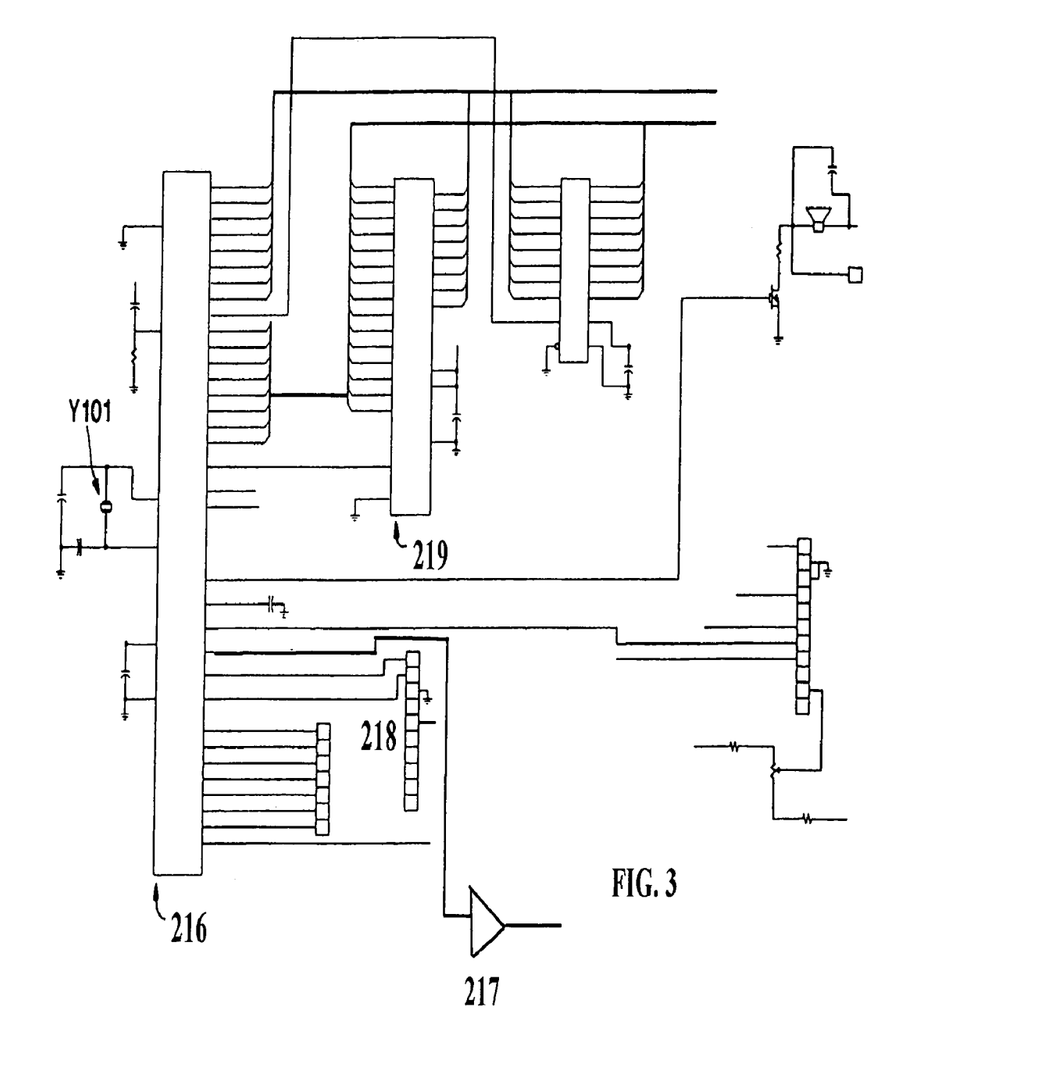
FIG. 3 is a schematic diagram of the micro-controller section used in the system.

The 360-degree sine wave is mathematically stored in 64 discrete steps in the PROM memory 219 FIG. 3. The micro-controller 216 retrieves the data, then by adjusting the timing between applying the steps to the multiplying Digital/Analog (D/A) converter 234 FIG. 5 the length of the stimulus is adjusted. Operational amplifier 235 FIG. 5 converts the output current of 234 FIG. 5 to produce a voltage output. Potentiometer 237 FIG. 5 adjusts the reference voltage, which adjusts the full-scale output current of Digital/Analog (D/A) converter 234 FIG. 5, therefore setting the full-scale output voltage of amplifier 235 FIG. 5. The full-scale output adjustment allows the output to be adjusted to the same output level of the switched capacitor filter 226 FIG. 4. Therefore no intensity conversion is necessary when switching between continuous full sinewave mode and 360 degree sine wave mode. The multiplexer 236 FIG. 5 selects whether the output is in continuous full sine wave mode or 360 degree sinewave mode.

Figure 4:
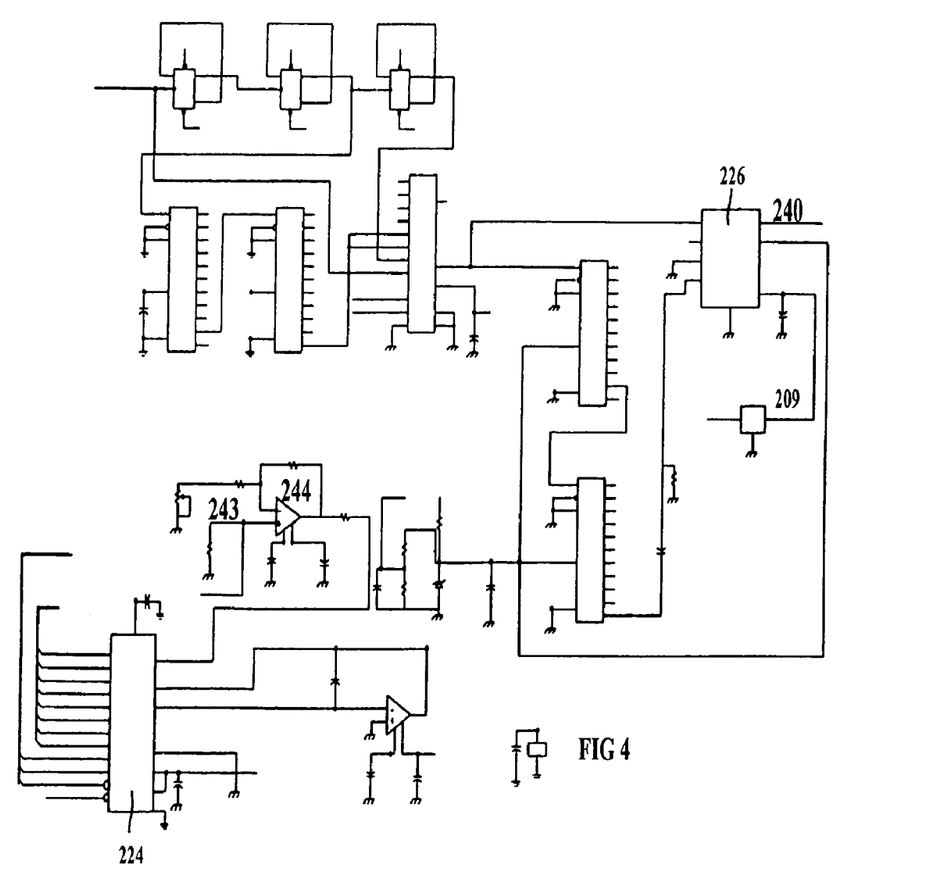
FIG. 4 is a schematic diagram of the waveform synthesizer used in the system.
Figure 5:
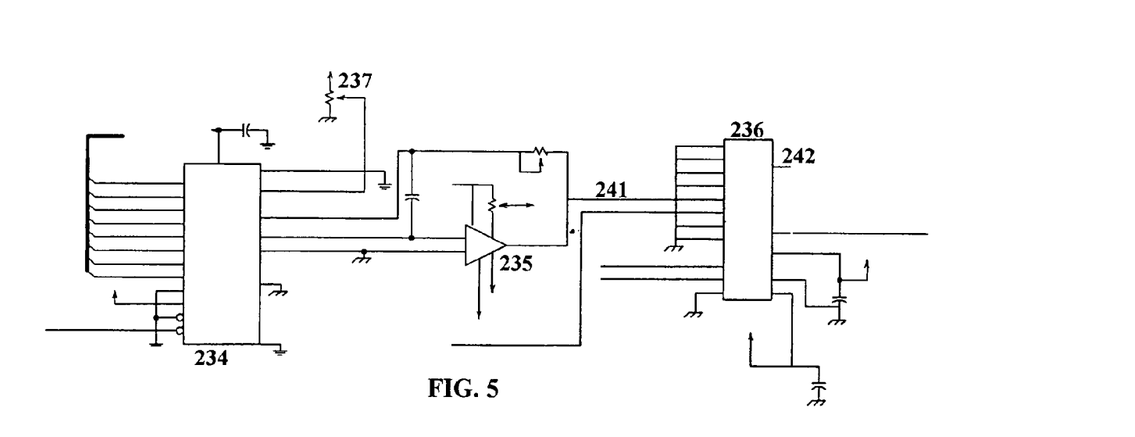
FIG. 5 is a schematic diagram of the 360-degree waveform synthesizer used in the system.

The duration of stimulus and timing of the presentation is controlled by a second crystal Y101 and the micro-controller 216 FIG. 3. The analog signal generated from the frequency synthesis section output 240 of FIG. 4 or 241 FIG. 5 is multiplexed by 236 FIG. 5. The output 242 FIG. 5 of the multiplexer 236 FIG. 5 is then applied to the input 243 FIG. 4 of amplifier 244 FIG. 4. The output of amplifier 244 FIG. 4 is applied to a multiplying Digital/Analog (D/A) converter 224 FIG. 4. The multiplying D/A converter 224 is a 12-bit unit. Therefore, it has 4096 individual steps. The device in the illustrated design uses the first 4,000 of these steps. For this example only 210 discrete codes are available to the user. After multiplying through the D/A converter 224 to set the selected amplitude, the sinewave produced is fed to a transconductance amplifier FIG. 6. The first section of the transconductance stage 227 creates two half copies of the signal, one is level shifted up to the high positive voltages and one is level shifted down to the high negative voltages. Current mirrors 245 and 246 FIG. 6, whose gains are approximately 6.2 are used to produce output currents from the two half signals, which are then combined at the output 229. The output current produced is a constant current regardless of the patients skin impedance, except of course when clipping has been indicated. The output signal then goes through an output relay 230 to the output jack 253.

Referring to FIG. 1, the LCD display 100 is directly driven off one of the micro-controller 216 ports as shown in FIG. 3. Referring to FIG. 3, this connection is a standard seven-line interface 218. The unit also provides an output for triggering other instruments 217 FIG. 3.

Figure 7:
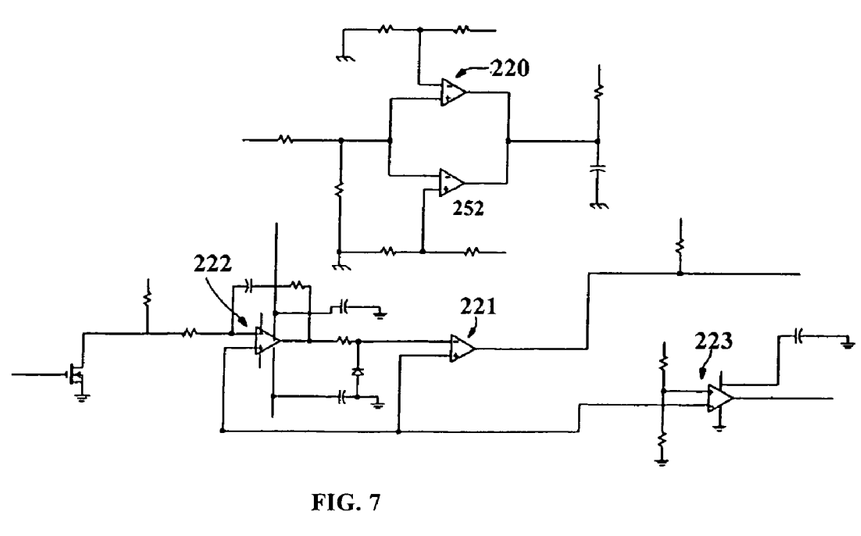
FIG. 7 is a schematic diagram of the Battery Integrator Schematic used in the system.

Referring to FIG. 7, the battery voltage monitoring function is a micro-controller 216 controlled dual slope integration technique using comparator 221 FIG. 7 and an operational amplifier 222 FIG. 7 to measure the battery 104 FIG. 1 voltage. Comparator 220 FIG. 7 and comparator 252 FIG. 7 provide clipping information. Comparator 223 FIG. 7 provides the battery discharge function.

Figure 8:
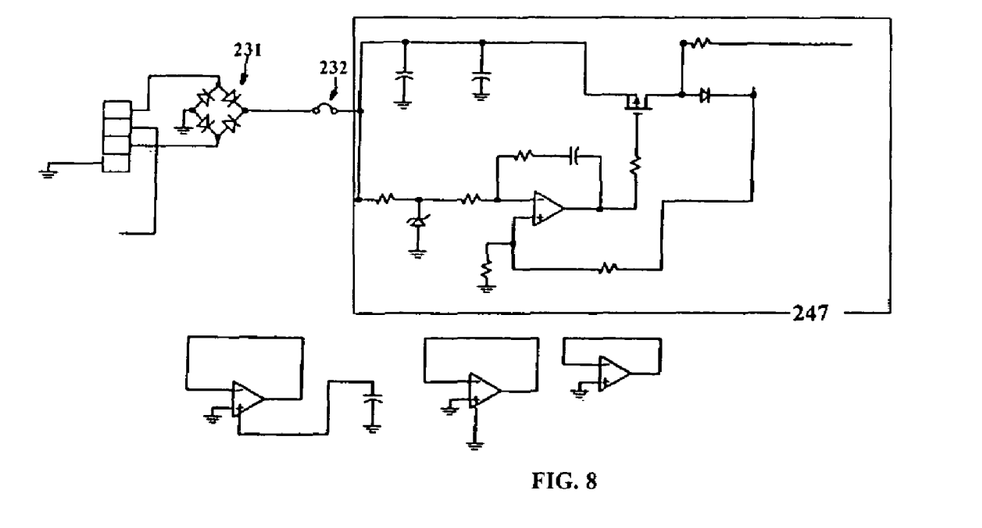
FIG. 8 is a schematic diagram of the battery charger circuit used in the system.

Referring to FIG. 8, the main board incorporates a battery charger circuit. A bridge rectifier 231 FIG. 8 is provided on the charger input. This allows the use of a charger with either center positive or center negative polarity. There is also a Polyfuse RTM. current limited device 232 FIG. 8 (manufactured by Raychem, USA), which takes the place of a fuse. The charger circuit FIG. 8 takes the raw unregulated voltage being provided by the charger unit 103 FIG. 1 and produces a precisely regulated 7 volt level for the battery 104 without the risk of overcharging, thereby significantly enhancing the life of the battery. The use of the bridge rectifier 231 FIG. 8 and internal regulator 247 FIG. 8 also allows a wide variety of chargers to be used with the unit. This simplifies the production of units for operational capability using the various types of voltages found in many parts of the world.

Figure 9:
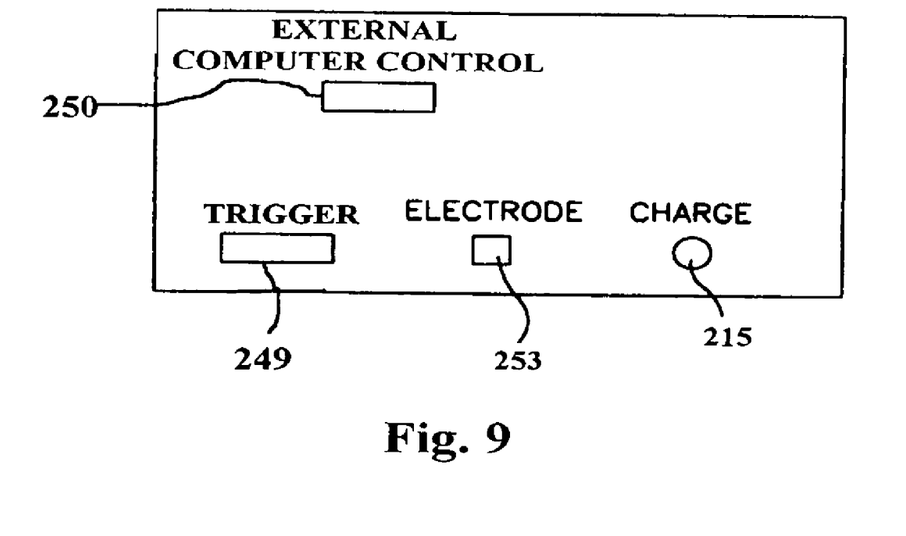
FIG. 9 is an illustration of the back panel of the device used in the system.

The of External Computer Control port 250 FIG. 9 is optically isolated. There is no Ohmic connection between the port and any subject circuitry. The External Computer control port 250 FIG. 9 is interfaced to the micro-controller 216 FIG. 3. This permits the attachment of an external computer 251 FIG. 1 to control or monitor the apparatus of the present invention/

This External Computer Control port 250 FIG. 9 utilizes a RS-232 chip set, a transformer for power, and four optical-isolators for data transfer all on separate circuit board for safety reasons. This design provides in excess of 2,500 Volts isolation. Therefore in the unlikely event of a power supply failure of an attached computer device while the subjects connected, safety is still maintained.

Alternatively the output of the device may be delivered an inductor to generate magnetic fields for electromagnetic stimulation.

FIG. 10 provides two illustrations of sine waveforms. The upper panel is a graph of amplitude vs time for the 2000 Hz and 5 Hz frequencies, depicting 2 kHz and 5 Hz waveforms drawn to scale. The lower panel is a graph of amplitude vs time for the 2000 Hz and 5 Hz frequencies, depicting both sinusoidal waveforms of the same intensity and this is not drawn according to scale.

The output stimulus of the present invention may also be utilized for analgesia evaluation, motor nerve block studies and other types of nerve conduction studies including H wave and F wave and Somatosensory Evoked Potential and EEG, EKG and other electrophysiological response related studies.

Although the present invention has been described in some detail by way of illustration and example for purposes of clarity and understanding, it will, of course, be understood that various changes and modifications may be made with the form, details, and arrangements of the parts without departing from the scope of the invention as set forth in the following claims.

The invention claimed is:

1. A method for evoking neuroselective responses from nervous tissue using electronic or electromagnetic stimulation that does not leave a sufficient voltage or electrical artifact on the tissue being stimulated that would interfere or prevent a monitoring system from recording the physiological response and which is also substantially painless in case the nervous tissue is in a living organism, or a method of in situ monitoring of nerve responses for evaluating the response to a therapeutic intervention, or a method for therapeutic nervous tissue stimulation including augmenting or attenuating normal or impaired nerve function, comprising attaching an electrode of an apparatus to the nervous tissue,
the apparatus comprising
an electrode which can be applied to nervous tissue of a patient effective for application thereto of electronic or electromagnetic stimulation having a waveform
a controller for controlling the waveform, duration and intensity of an electronic or electromagnetic stimulation that is applied to nervous tissues through said electrode and does not leave a sufficient voltage or electrical artifact on the tissue being stimulated that would interfere or prevent a monitoring component from recording a physiological response of said tissue to said stimulation, and a monitoring component that monitors the physiological response of said nervous tissue, the apparatus a) being capable of generating an electronic or electromagnetic stimulation that has a single 180° or 360° sine waveform, or b) being capable of generating an of electronic or electromagnetic sine wave stimulation that has a duration of less than 200 ms, providing a stimulation that has a single 180° or 360° sine waveform, or a sine wave form with a duration of less than 200 ms, with said apparatus, and monitoring the physiological response of the nervous tissue with said apparatus.

2. A method according to claim 1, wherein the stimulation has a single 180° or 330° sine waveform.

3. A method according to claim 1, wherein in the apparatus the monitoring component comprises a recording component for recording the physiological response of said nervous tissue, and an output trigger to the recording component.

4. A method according to claim 1, wherein in the apparatus the electronic or electromagnetic stimulation is generated by programmable circuitry.

5. A method according to claim 1, wherein the apparatus is comprised in a NCV, nervous tissue monitor or Current Perception Threshold (CPT) apparatus.

6. A method according to claim 1, wherein in the apparatus the controller and the monitoring component is an external computer.

7. A method according to claim 1, wherein the apparatus further comprises a quartz crystal for timing of the stimulation.

8. A method according to claim 1, wherein the stimulation has a constant current.

9. A method according to claim 1, wherein the stimulation has a frequency of 2000 Hz.

10. A method according to claim 1, wherein the stimulation has a frequency of 5 Hz.

11. A method according to claim 1, wherein the stimulation is repeatedly administered to permit the averaging of the physiological response of a patient.

12. A method according to claim 1, which is for evoking neuroselective responses from nervous tissue using electronic or electromagnetic stimulation that does not leave a sufficient voltage or electrical artifact on the tissue being stimulated that would interfere or prevent a monitoring system from recording the physiological response and which is also substantially painless in case the nervous tissue is in a living organism.

13. A method according to claim 12, wherein the frequency of the stimulation is 5 to 2000 Hz.

14. A method according to claim 12, wherein the nervous tissue is in a human, or in an animal or is isolated nervous tissue.

15. A method according to claim 12, wherein physiological response of the nervous tissue is monitored by making nerve conduction velocity and amplitude measurements.

16. A method according to claim 1, which is of in situ monitoring of nerve responses for evaluating the response to a therapeutic intervention.

17. A method according to claim 12, wherein the nervous tissue is spinal cord tissue or a prosthetic nerve.

18. A method according to claim 1, which is for therapeutic nervous tissue stimulation including augmenting or attenuating normal or impaired nerve function.

19. A method according to claim 1, wherein the stimulation has a sine wave form with a duration of less than 200 ms.

* * * * *